US012508257B2

(12) United States Patent
Hille et al.

(10) Patent No.: US 12,508,257 B2
(45) Date of Patent: Dec. 30, 2025

(54) METHOD FOR PRODUCING ACTIVE AGENT ADMINISTERING SYSTEMS BY MEANS OF PAD PRINTING PROCESSES

(71) Applicant: LTS LOHMANN THERAPIE-SYSTEME AG, Andernach (DE)

(72) Inventors: Thomas Hille, Neuwied (DE); Petra Botzem, Andernach (DE); Albert Wionzek, Rüscheid (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 953 days.

(21) Appl. No.: 17/622,531

(22) PCT Filed: Jun. 26, 2020

(86) PCT No.: PCT/DE2020/100558

§ 371 (c)(1),
(2) Date: Dec. 23, 2021

(87) PCT Pub. No.: WO2020/259765

PCT Pub. Date: Dec. 30, 2020

(65) Prior Publication Data

US 2022/0370433 A1 Nov. 24, 2022

(30) Foreign Application Priority Data

Jun. 27, 2019 (DE) ..................... 10 2019 117 310.8

(51) Int. Cl.
*A61K 31/465* (2006.01)
*A61K 9/70* (2006.01)

(52) U.S. Cl.
CPC .......... *A61K 31/465* (2013.01); *A61K 9/7084* (2013.01)

(58) Field of Classification Search
CPC ............................ A61K 31/465; A61K 9/7084
See application file for complete search history.

(56) References Cited

U.S. PATENT DOCUMENTS 5,110,599 A 5/1992 Anhauser et al.
2008/0233177 A1 9/2008 Meconi
2020/0230074 A1 7/2020 Hille et al.

FOREIGN PATENT DOCUMENTS

WO 1989001328 A1 2/1989
WO 2006094681 A1 9/2006
WO 20180153413 A1 8/2018

OTHER PUBLICATIONS

International Search Report for Application No. PCT/DE2020/100558, Mailed Oct. 7, 2020, 3 pages.
PCT/IPEA/409 dated May 27, 2021, 15 pages.

*Primary Examiner* — Shirley V Gembeh
(74) *Attorney, Agent, or Firm* — Lippes Mathias LLP

(57) ABSTRACT

The present invention relates to a pad printing method for producing an administration form for a pharmaceutical active agent, wherein the method comprises providing a substrate of the administration form and transferring the active agent by means of a pad from a cliché onto the substrate, wherein the area of the cliché is larger than the active-agent-containing area printed onto the substrate. This method is especially suitable for producing transdermal therapeutic systems with volatile active agents. The present invention also relates to arrangements by means of which a method of this kind can be implemented.

16 Claims, 2 Drawing Sheets

Figure 1:
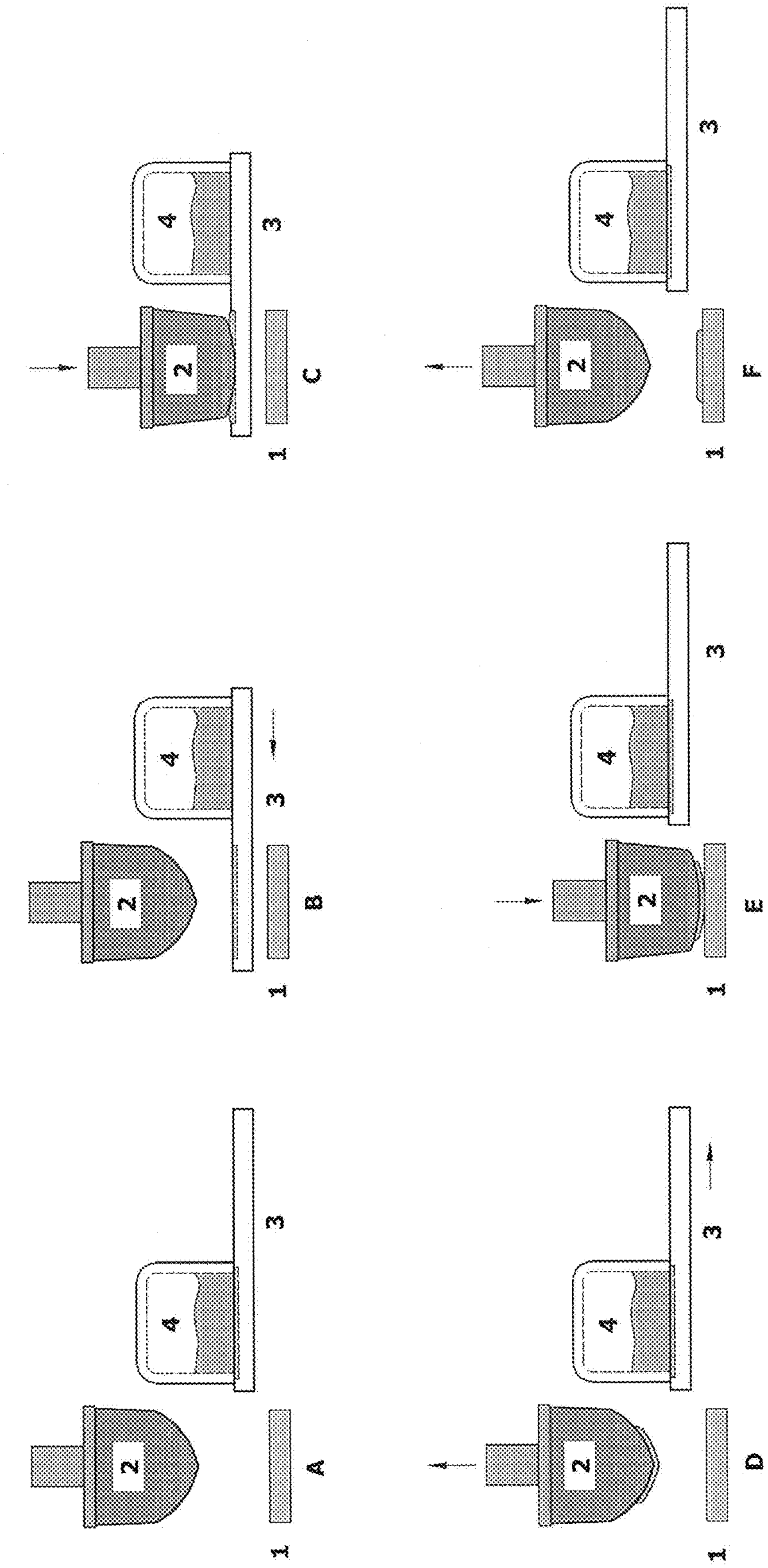

METHOD FOR PRODUCING ACTIVE AGENT ADMINISTERING SYSTEMS BY MEANS OF PAD PRINTING PROCESSES

The present invention relates to a method for producing active agent administering systems by means of pad printing processes for transferring defined amounts of print medium per unit of area, and to device arrangements for producing such active agent administering systems.

Pad printing is an indirect gravure printing method in which the printing ink is transferred by an elastic pad made of silicone rubber from the printing plate to the substrate to be printed or the print substrate. Pad printing methods have been known for many decades and are suitable especially for printing uneven surfaces since the flexible pad which transfers the print medium can easily adapt to the substrate surface. A pad printer is described for example in DE 19 39 437 A1.

A cliché is used for pad printing, wherein this cliché is a printing plate which is etched in on a substrate in a recessed manner and in which the print medium or the printing ink is held ready. To fill the cavities of the cliché, the print medium is firstly applied to the cliché and is subjected to a doctoring process, which doses and levels the print medium received in the cliché. The print medium layer remaining in the indentation of the cliché is fully received by the pad by pressing this on and is transferred to the object to be printed.

An overview of applications and properties of the pad printing method can be found in the brochure from the company TAMPOPRINT GmbH, Daimlerstraße 27/1 in Korntal-Münchingen and in document DE OS 1939437, to which reference is made fully in order to avoid repetitions.

Pad printing systems are very advantageous due to their small spatial requirement, since they can be integrated and also encapsulated without difficulty in production lines, which is of considerable advantage when processing highly effective or toxic print media, such as active ingredients, etching inks, polymerisation starters or the like, so as to protect the operating personnel, but also so as to reduce the vaporisation of volatile substances.

A transdermal therapeutic system (TTS) is an application system for a pharmaceutical active agent, in which the active agent is delivered transdermally to the patient. The most common form of transdermal therapeutic systems is a patch containing the active agent, which patch is adhered to the skin and from which the active agent is then absorbed by resorption through the skin.

At the start of TTS development, it was assumed that an implementation of active agents in transdermal therapeutic systems is generally unproblematic, and that this application form can be used for a large number of active agents. This assessment, however, has since proven to be a fallacy.

The production of TTS with active agents with high vapour pressure, such as especially nicotine or essential oils such as linalool, is additionally problematic on account of the volatility of the active agents, since these at least partially vaporise within the scope of the standard method for producing TTS constituted by "coating adhesive solutions on films" and "channel drying". Nowadays, TTS with volatile active agents are produced by laying cotton fleece or paper blanks by machine onto laminates consisting of adhesive matrices and removable protective film, onto which blanks the active agent is then printed, optionally in the form of a solution. By way of example, reference can be made here to DE 36 29 304 A1 or EP 3 145 501 A1, in which nicotine solutions and lavender oil respectively are printed onto a paper substrate. The adhesive webs with the printed blanks are then covered with laminates made of adhesive matrices on films, in order to obtain a TTS in which the active agent is embedded between matrices on protective and backing layers. The TTS are then stamped into the appropriate format, separated and packaged.

The pad printing method has the additional advantage that production losses of active-agent-containing laminate are avoided; usually, grids are produced when the TTS are stamped into the appropriate format and separated, which grids are discarded when TTS are not produced by printing methods. This is not applicable in the case of pad printing on paper blanks, since these blanks lie on adhesive webs and active-agent-free areas protrude beyond the blanks on all sides. The stamping is then performed in the active-agent-free regions, so that the grids discarded when separating the TTS are free from active agent. Highly toxic production waste can thus be avoided in pad printing methods.

Nowadays, pad printing systems are used for example for the production of TTS for delivering nicotine, such as Nicotinell®, Nicofrenon®, and Nicopatch® or Habitrol® These printing methods are described in industrial property rights DE OS 37 27 214 A1 and EP 0303025. In practice, however, it has been found that raw surfaces, such as fleece or paper, can be printed reproducibly with the pad printing method proposed in DE 37 27 214 A1, however, direct printing of pressure-sensitive adhesives was not possible. The mentioned industrial property rights indeed describe the production of TTS without cotton fleece or paper, however, when attempting to reproduce TTS by the methods disclosed in the documents it was found that printing media were not transferred fully to the object to be printed, contrary to the indications, for example, in DE OS 37 27 214. The same is true for EP 1 855 660 A1. Due to these production problems, the pad printing method has not yet become established, for example, for the production of nicotine TTS.

All of the above-mentioned commercial nicotine TTS contain paper, which replaced the cotton fleeces used initially. Paper or fleeces can indeed be printed without difficulty due to their absorbency, however, due to their structure they have the disadvantage of air inclusions, which result in problems relating to stability, especially in the case of active agents that are highly sensitive to oxidation, such as nicotine or linalool. When nicotine breaks down, myosin may be created, which is perceived as a discolouration. In addition, the paper itself may contain discolorations. In order to avoid any uncertainty on the part of the consumer in respect of whether the TTS is still usable, aluminised and lacquered films are therefore generally used, which are relatively costly. The avoidance of paper or other absorbent substrate types therefore not only has significant advantages for patient certainty, but also allows a significant cost reduction of the medicinal product.

According to the above, there was thus a need for a production method for transdermal therapeutic systems with which on the one hand the advantages of the pad printing method can be realised for the production of TTS containing relatively volatile active agents, without the TTS containing, for this purpose, an absorbable layer formed from cotton fleece or paper.

The aim of the invention was consequently to further develop the known methods in such a way that even TTS containing volatile active ingredients can be produced neatly and reliably by means of the very robust pad printing method, if the substrate to be printed is not absorbent, i.e., for example, is present in the form of a pressure-sensitive adhesive. It must be ensured here that the dosing satisfies the requirements on medicinal products and that production downtimes are avoided to the greatest possible extent. If too little active agent solution is transferred, such downtimes would be frequent, since active agent solution remaining on the pad would cause the indentation of the cliché to overflow when the cliché is dipped again, which would necessitate a comprehensive cleaning of the cliché.

The aim has been addressed in accordance with the invention by adjusting the geometry of the printing cliché, which is characterised in that the area of the indentation of the cliché is larger than the area of the active-agent-containing imprint. This solution is even more surprising because the problem was not described in the prior art, although the teaching of the invention represents a contribution to pharmaceutical drug safety, especially since the oxygen sensitivity of the natural products nicotine or linalool and the subsequent need to avoid materials that have air inclusions has long been known. There was a preconception, however, that only the printing of absorbent substrates leads to pharmaceutically acceptable active agent contents. Comparative examples 1-8 (see below) support this hypothesis.

The term "pad printing" within the scope of this invention shall be understood to mean an indirect gravure printing method in which the "printing ink" (which, within the scope of the invention, is an active-ingredient-containing solution) is transferred by an elastic pad made of silicone rubber from the printing plate onto the print substrate (or in the present case preferably onto a pressure-sensitive adhesive).

A "pharmaceutical active agent" shall be understood to mean substances and preparations of substances which are used to cure or alleviate illnesses or which ensure that illnesses or pain do not occur in the first place (prophylaxis). This is true both for the use in humans and in animals. The substances can act here in the body or also on the body.

The pharmacologically acting substance (active substance) can be different from the pharmaceutical active agent contained in the medicinal product. The pharmacologically acting substance, for example to increase the solubility, can thus be incorporated in the form of its salt into the US, or a precursor substance ("prodrug") can be used, which only becomes active after metabolisation. A typical metabolisation mechanism is, for example, the saponification of esters into the alcohols or acids which are then pharmacologically effective.

"Transdermal therapeutic systems" (US), in accordance with the invention, are patch-like medicinal products, which, similarly to plasters, are applied externally and which generally have an active-agent-impermeable backing layer, an adhesive layer, which can contain the active agent (which alternatively, however, can also be present in further separate layers), and optionally a removable protective layer.

In contrast to adhesive plasters or first-aid dressings, US contain an active ingredient which, during the application of the TTS, is absorbed through the skin and is distributed within the body via the bloodstream and provides its effect centrally. US have become widespread in recent years as a dosage form for the treatment of numerous diseases, since they are associated with many advantages as compared to conventional administration forms. These consist, inter alia, of a precise and constant active agent delivery, which is necessary for a constant concentration of the active substance in the blood plasma. In addition, the first-pass effect can be avoided and the compliance can be increased, since the patient does not have to take tablets at regular intervals. One advantage of transdermal therapeutic systems over other topical application systems, such as ointments or creams, lies in the fact that they can be applied over a precise area and thus with a precise dosing, without risk of the ointment being wiped off accidentally or other areas of skin being contaminated. In addition, ointments or tablets have to be administered regularly, since it is not generally possible to provide a delayed release of the active agent.

A first aspect of the present invention relates to a pad printing method for producing an administration form for a pharmaceutical active agent, wherein the method comprises the steps of providing a substrate of the administration form and transferring the active agent by means of a pad from a cliché onto the substrate, wherein the area of the indentation of the cliché is larger than the active-agent-containing area printed onto the substrate.

The feature "wherein the area of the indentation of the cliché is larger than the active-agent-containing imprint on the substrate" can be realised, for example, in that the size of the pad is smaller than the size of the indentation of the cliché so that, when the pad is fully dipped in the indentation of the cliché, there is a remaining part protruding beyond at the edge of the indentation, which is not covered by the pad. On the other hand, however, with a pad that is the same size as or larger than the indentation of the cliché, the feature can also be realised in that the pad is pressed into the cliché during the method only to such an extent that there is a remaining part of the cliché protruding with respect to the cliché/pad contact area.

It is expedient if the active-agent-containing imprint is produced by pressing the pad onto the substrate to such an extent that the area of the pad covered previously by the pharmaceutical active agent rests fully on the substrate.

It is furthermore preferred if the indentation of the cliché is circular and has a diameter which is at least 1.5 mm, preferably at least 2.0 mm, and especially preferably at least 3 mm larger than the diameter of the active-agent-containing imprint printed onto the substrate. On the whole, the indentation of the cliché preferably has a diameter of at least 31 mm, more preferably lies in the range of 31.5 mm and 35 mm, and more preferably in the range of 32 mm and 33 mm. For the area of the indentation of the cliché, an area in the range of 7 $cm^2$ to 10 $cm^2$ is suitable, and an area in the range of 8 $cm^2$ to 9 $cm^2$ is preferred. The area of the imprint generated by means of the method is preferably 6 $cm^2$ to 8 $cm^2$ and especially preferably 6.5 $cm^2$ to 7.5 $cm^2$. Alternatively, the indentation of the cliché preferably has a diameter of at least 42 mm to 55 mm and preferably 45 mm to 49 mm; in this case a printed image with a diameter of approximately 40 mm would expediently be produced. Further alternatively, the indentation of the cliché preferably has a diameter of at least 51 mm to 60 mm and preferably 53 mm to 56 mm; in this case a printed image with a diameter of approximately 49 mm would expediently be produced. Generally, the indentation of the cliché should have a diameter that is at least 8%, and preferably at least 10% larger than the diameter of the printed image, and a value of 20% and preferably 18% can be stated as an expedient upper limit.

The method is lastly further expediently configured in that it has a plurality of steps of transferring the active agent by means of a pad from a cliché to the substrate, wherein the active agent is transferred in each case to a fresh substrate.

A preferred administration form for production by the stated method is a transdermal therapeutic system (TTS).

The pharmaceutical active agent is preferably one or more naturally occurring active ingredients (natural products) as well as the partially synthetic derivatives thereof and chemical active ingredients thereof produced by total synthesis. Alternatively, an active ingredient produced by biotechnology can also be used, and these are gaining in importance.

Pharmaceutical active agents that have a boiling point of at most 250° C. at a pressure of 101.3 kPa are preferred within the scope of the present invention, since it is not possible to produce these by means of the standard method for producing transdermal therapeutic systems due to the vaporisation problem. According to Directive 2004/42/EC of 21 Apr. 2004, organic compounds with an initial boiling point of at most 250° C. at a standard pressure of 101.3 kPa are considered to be volatile.

In an especially preferred embodiment, the pharmaceutical active agent comprises nicotine; the pharmaceutical active agent is very especially preferably nicotine. Nicotine has a boiling point of 247° C. and a vapour pressure at 20° C. of 5.6 Pa.

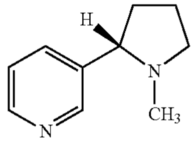

In a further preferred embodiment, the pharmaceutical active agent is an essential oil or an ester thereof, or mixtures of such essential oils or esters thereof. The essential oil especially preferably contains linalool. Alternatively, the pharmaceutical active agent can also comprise linalool or the pharmaceutical active agent can be linalool. Linalool has a boiling point of 198° C. and a vapour pressure at 20° C. of 10 Pa.

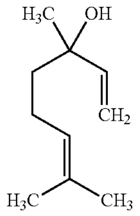

Due to the double bonds, linalool is especially sensitive to oxidation.

Due to their classification pursuant to Directive 2004/42/EC as volatile and owing to their sensitivity to oxidation, nicotine and linalool are especially suitable for the production method for TTS according to the invention.

The present invention is not subject to any relevant limitations in respect of the structural design of the transdermal therapeutic systems to be produced by means of the method, and therefore these can be relatively simple systems, which consist only of an active-agent-impermeable backing layer and adhesive layer (in which the active agent is present or with which it is in contact), as well as optionally a removable protective layer, or more complex systems with a plurality of bonding or adhesive layers and active-agent-containing layers.

The active agent within the scope of the invention is preferably not present in a layer that is formed by or comprises an absorbent substrate, such as a cotton fleece or a paper. In the method according to the invention it is consequently preferred if the pharmaceutical active agent is not applied to such a substrate. An “absorbent substrate” is understood here to mean a substrate that is porous at its surface and in the pores of which the applied active agent is absorbed.

It is preferred in accordance with the invention if the substrate to which the pharmaceutical active agent is applied by means of a pad has an upper layer formed of adhesive. This adhesive is especially preferably a pressure-sensitive adhesive, and especially a pressure-sensitive polyacrylate adhesive.

It is furthermore or alternatively preferred if the pharmaceutical active agent is formulated for transfer to the substrate comprising an adhesive, preferably a pressure-sensitive adhesive, and especially preferably comprising a polyacrylate adhesive. The proportion of the adhesive in this case, where possible, should not be greater than 80 wt. %, preferably not more than 60 wt. %. An adhesive proportion of 20 to 50 wt. % is especially preferred.

In order to improve the stability, the adhesive of the substrate or in the formulation containing the pharmaceutical active agent can contain a crosslinking agent, such as a Lewis acid, especially based on aluminium or titanium, which are known to a person skilled in the art of adhesives.

Furthermore, the adhesive of the substrate or in the formulation containing the pharmaceutical active agent can contain conventional modifiers, for example in the form of medium-chain triglycerides.

Within the scope of the method according to the invention it is possible, subsequently to applying the active agent or the active-agent-containing formulation, to cover the active agent with a suitable layer, such as a further adhesive layer or a multi-layer substrate.

The active-agent-impermeable backing layer can be a material that is usual for this purpose, for example polyethylene terephthalate, expediently with a layer thickness sufficient for this purpose, for example in the range of 5 to 70 μm or 20 to 50 μm, which can also be transparent.

A further aspect of the present invention relates to an administration form for a pharmaceutical active agent which can be produced by a method as described hereinbefore and which contains a pharmaceutical active agent with a boiling point of at most 250° C. at a pressure of 101.3 kPa. This administration form is preferably a transdermal therapeutic system. It is preferred here if the one administration form is present in the form of a plurality of individual administration forms (i.e. as a batch), which is obtainable from a production process performed after the above-described method and in which the individual administration forms have a substantially uniform active agent content. The term “substantially” denotes here a possible deviation of the active agent content of less than 5 wt. %, preferably less than 2 wt. %, and especially preferably less than 1 wt. %. A “plurality” of individual administration forms are preferably more than 10 and especially preferably more than 100.

A further aspect of the present invention relates to a transdermal therapeutic system comprising an active-agent-impermeable backing layer, a substrate layer, an active-agent-containing layer, and optionally a removable protective layer, wherein the active-agent-containing layer contains a pharmaceutical active agent with a boiling point of at most 250° C. at a pressure of 101.3 kPa and does not comprise a porous substrate.

Substrates such as paper or nonwovens, which are porous per se, are considered to be porous substrates, but not materials that are theoretically porous, because they contain a particulate constituent, the removal of which would result in a porous material. A porous material is thus able to absorb another material in its pores.

For the described transdermal therapeutic system, it is preferred if the pharmaceutical active agent is present in the form of nicotine or linalool, or if these are at least part of the pharmaceutical active agent.

A further aspect of the present invention relates to an arrangement for applying an active agent to a substrate with the aid of a pad printing system comprising a device for pad printing with a pad and a cliché, wherein the indentation of the cliché is filled at least in part with an active-agent-containing formulation, and wherein the arrangement has a substrate for receiving the active-agent-containing formulation from the pad from the device. The device is adapted here such that the contact area of the pad in the cliché is smaller than the area of the indentation of the cliché.

As already explained for the method according to the invention, the device adapted in respect of the contact area of the pad in the cliché can be adapted such that the pad is smaller than the area of the indentation of the cliché, however, it is also possible that the adaptation is performed such that the control device of the pad is set such that the pad is pressed into the cliché during the method only to such an extent that there is a remaining part of the cliché that protrudes with respect to the cliche/pad contact area. In this case it is possible that the pad is the same size as or even larger than the cliché.

In a preferred embodiment the arrangement furthermore comprises a storage container for storing the active-agent-containing formulation and means for introducing the formulation into the cliché. These means expediently also include means for scraping off protruding residues of active-agent-containing formulation from the cliché, for example a doctor blade.

With regard to the pharmaceutical active agents to be incorporated into the active-agent-containing formulation, the pharmaceutical active agents stated as being preferred in conjunction with the method according to the invention are also considered to be preferred in the arrangement. The same is true for the absorption of the active-agent-containing formulation by the pad.

Consequently, it is preferred for the arrangement if this contains in the active agent-containing formulation an active agent with a boiling point of at most 250° C. at a pressure of 101.3 kPa, preferably in the form of nicotine or linalool. It is also preferred if the substrate in the arrangement does not have an absorbent substrate on its upper side.

Figure 2:
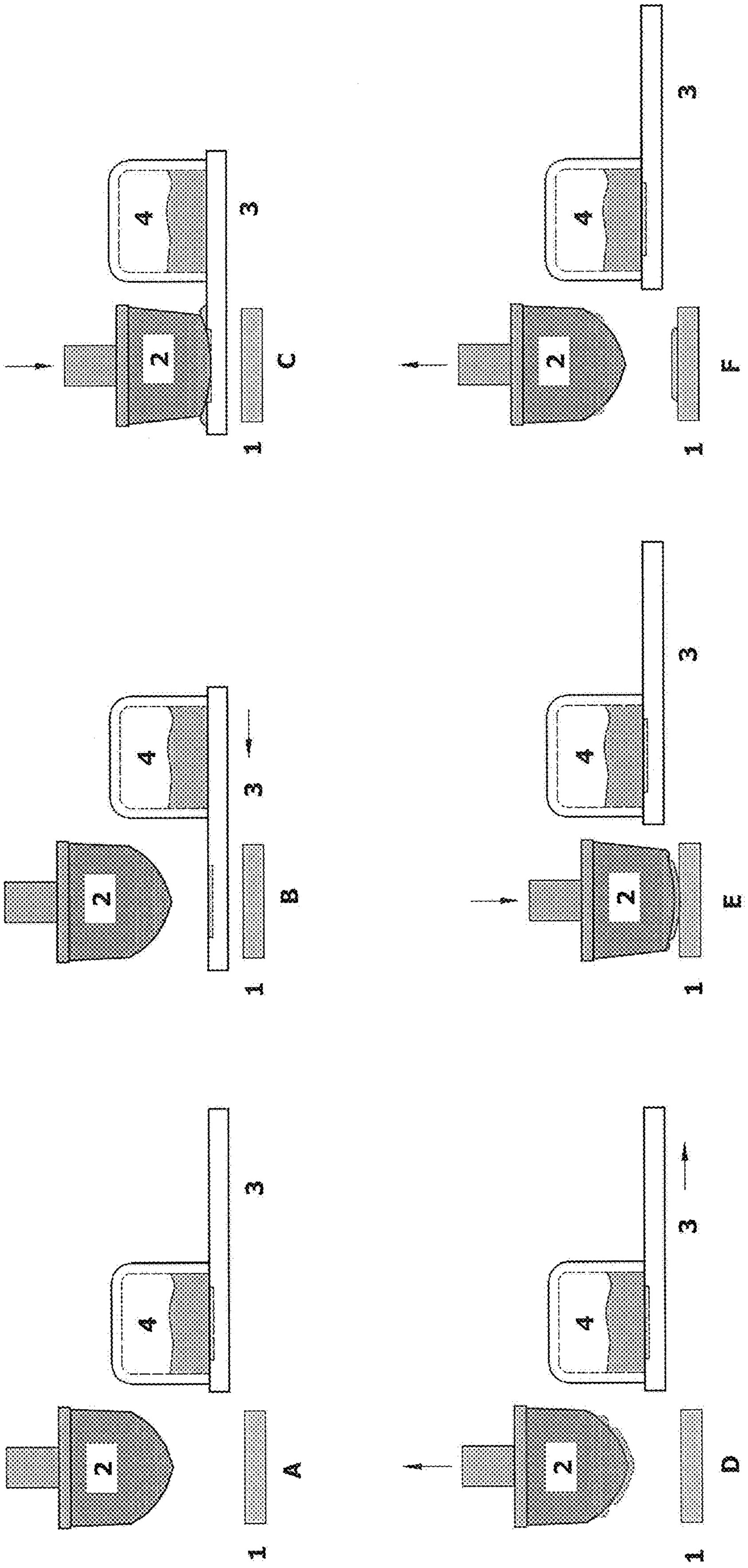

FIGS. 1 and 2 show, for further illustration of the method according to the invention, a method according to the prior art (FIG. 2) and a method according to the teaching of the invention (FIG. 1). Both methods proceed from a substrate 1 and a device comprising a pad 2 and a cliché 3, which contains an active-agent-containing solution 4 in the indentation of the cliché (A). The cliché with the active-agent-containing solution is then brought into position beneath the pad (B) and the pad is dipped into the indentation of the cliché (C). The pad is then lifted again from the cliché and is returned to its original position (D). The pad with the active agent is then brought to rest on the substrate (E) and is lifted again (F), wherein the active agent is transferred to the substrate.

The invention will be illustrated in greater detail hereinafter with reference to the following examples, which are not in any way intended to limit the scope of protection.

EXAMPLES

All examples were produced in accordance with the following provisions:

The amounts specified in Table 1 of nicotinic basic polymethacrylate solution (41.7% basic polymethacrylate, 58.3% nicotine) were printed with the aid of a pad printing system onto a laminate consisting of a lowermost removable polyethylene terephthalate (PET) film 100 μm thick, a skin contact layer formed from 98% polyacrylate and 2% medium-chain triglycerides (40 $g/m^2$ weight per unit area) and an adhesive layer formed from 78% polyacrylate, 20% basic polymethacrylate and 2% medium-chain triglycerides (220 $g/m^2$ weight per unit area). The adhesive surface was printed here directly. The printed adhesive surface was then covered by the adhesive surface of a laminate formed from an adhesive layer formed from 78% polyacrylate, 20% basic polymethacrylate and 2% medium-chain triglycerides (110 $g/m^2$ weight per unit area) on a polyethylene terephthalate (PET) film 15 μm thick. TTS formats were then stamped, and the TTS were separated.

TABLE 1

Comparative examples according to the prior art versus results according to the teaching of the invention

| Example no. | TTS area | Pad hardness | Cliché depth [μm]/ diameter [mm] | Printed image diameter [mm] | Material application [mg] according to gravimetric IPK |
|---|---|---|---|---|---|
| 1* | 10 $cm^2$ TTS/30 mg | 3 shore (pointed) | 162.5/27 | Not determined since weight not reached | 21.8-22.0 weight not reached |
| 2* | 10 $cm^2$ TTS/30 mg | 3 shore (pointed) | 180/27 | Not determined since weight not reached | 25.9 weight not reached |
| 3* | 10 $cm^2$ TTS/30 mg | 3 shore (pointed) | 190/27 | 27 | 27.9-28.6 "dry rubber imprint" visible on the web |
| 4* | 10 $cm^2$/30 mg | 3 shore (pointed) | 190/27 | Not determined since weight not reached | 27.5-27.7 "dry rubber imprint" visible on the web |

TABLE 1-continued

Comparative examples according to the prior art versus results according to the teaching of the invention

| Example no. | TTS area | Pad hardness | Cliché depth [μm]/ diameter [mm] | Printed image diameter [mm] | Material application [mg] according to gravimetric IPK |
|---|---|---|---|---|---|
| 5* | 10 $cm^2$/30 mg | 3 shore (rounded) | 190/27 | Not determined since weight not reached | 26.8-27.0 "dry rubber imprint" visible on the web, many splashes |
| 6* | 10 $cm^2$/30 mg | 3 shore (pointed) | 210/27 | 27 | 28.1-28.6 "dry rubber imprint" visible on the web |
| 7* | 10 $cm^2$ TTS/30 mg | 9 shore (pointed) | 200/27 | 27 | 29.0-31.1 Very large amount of excess material on cliché and slide |
| 8* | 10 $cm^2$/30 mg | 3 shore (pointed) | 180/27 | Not determined since weight not reached | 25.9 weight not reached |
| 9[1] | 10 $cm^2$ TTS/30 mg | 6 shore | 162.5/32 | 29-30.0 | 29.3-30.9 |
| 10[1] | 10 $cm^2$ TTS/30 mg | 3 shore | 162.5/32 | 29-31.0 | 29.7-30.9 |
| 11[1] | 20 $cm^2$ TTS/60 mg | 6 shore | 175/49 | 40-41.5 | 58.0-61.1 |
| 12[1,2] | 20 $cm^2$ TTS/60 mg | 6 shore | 175/49 | 40-41.5 | 59.0-60.6 |
| 13[1] | 30 $cm^2$ TTS/90 mg | 6 shore | 180/56 | 47-49 | 86.6-90.4 |
| 14[1,3] | 30 $cm^2$ TTS/90 mg | 6 shore | 180/56 | 47-49 | 88.2-92.0 |

*= prior art;
[1]= according to the invention;
[2]= repeat of 11;
[3]= repeat of 13

The prior art products were produced in accordance with the general provisions from OS DE 37 27 214 and EP 0 303 025.

In comparative examples 1, 2, 4, 5 and 8, only an insufficient material application was achieved. In comparative examples 3, 6 and 7, a material application satisfying the pharmaceutical requirements was achieved. In these examples, however, significant production problems were encountered, because the adhesive surface did not take on the entire nicotine solution that had been transferred to the pad. As a result, the residues still remaining on the pad after the printing process formed a protrusion and extended beyond the surface of the cliché indentation.

This is avoided by the geometry, i.e. by the larger cliché diameter in comparison to the printed image, as shown in Examples 9-14; no production problems were observed in these cases.

The invention claimed is:

1. A pad printing method for producing an administration form for a pharmaceutical active agent, comprising providing a non-absorbent substrate of the administration form and transferring the active agent by means of a pad from a cliché onto the non-absorbent substrate, wherein the area of the indentation of the cliché is larger than the area of the active-agent-containing imprint printed onto the non-absorbent substrate.

2. The pad printing method according to claim 1, characterised in that the cliché is circular and has a diameter which is at least 5 mm larger than the diameter of the active-agent-containing imprint printed onto the non-absorbent substrate.

3. The pad printing method according to claim 1, characterised in that the administration form is a transdermal therapeutic system (TTS).

4. The pad printing method according to claim 1, characterised in that the non-absorbent substrate to which the pharmaceutical active agent is applied by means of a pad has an upper layer formed from adhesive to which the active agent is applied.

5. The pad printing method according to claim 4, characterised in that the pharmaceutical active agent is formulated for the transfer onto the non-absorbent substrate comprising an adhesive in the form of a polyacrylate adhesive.

6. The pad printing method according to claim 5, characterised in that the adhesive is a pressure sensitive adhesive.

7. The pad printing method according to claim 1, characterised in that the pharmaceutical active agent has a boiling point of at most 250° C. at a pressure of 101.3 kPa.

8. The pad printing method according to claim 7, characterised in that the pharmaceutical active agent is present in the form of nicotine.

9. The pad printing method according to claim 7, characterised in that the pharmaceutical active agent is present in the form of a mixture of essential oils or contains an essential oil or an ester thereof.

10. The pad printing method according to claim 7, characterised in that the printed active agent is then covered by an active-agent-impermeable backing layer.

11. The pad printing method according to claim 1, characterised in that the cliche is circular and has a diameter which is at least 10 mm larger than the diameter of the active-agent-containing imprint printed onto the non-absorbent substrate.

12. The pad printing method according to claim 1, characterised in that the cliche is circular and has a diameter which is at least 25 mm larger than the diameter of the active-agent-containing imprint printed onto the non-absorbent substrate.

13. An arrangement for applying an active agent to a non-absorbent substrate with the aid of a pad printing system, comprising a device with a pad and a cliché, wherein the cliché is filled at least in part with an active-agent-containing formulation, and a non-absorbent substrate for receiving the active-agent-containing formulation from the pad from the device, wherein the device is adapted such that the contact area of the pad is smaller than the area of an indentation of the cliché.

14. The arrangement according to claim 13, comprising a storage container for storing the active-agent-containing formulation and means for introducing the formulation into the cliché.

15. The arrangement according to claim 13, wherein the active-agent-containing formulation contains an active agent with a boiling point of at most 250° C. at a pressure of 101.3 kPa.

16. The arrangement according to claim 13, wherein the active agent is in the form of nicotine.

* * * * *